United States Patent [19]
Okazaki et al.

[11] Patent Number: 6,020,464
[45] Date of Patent: Feb. 1, 2000

[54] ISOLATED SMAD PROTEIN

[75] Inventors: Kenji Okazaki, Minoo; Koki Kitamura, Suita, both of Japan

[73] Assignee: Biomolecular Engineering Research Institute, Osaka, Japan

[21] Appl. No.: 09/063,893

[22] Filed: Apr. 22, 1998

[30] Foreign Application Priority Data

Apr. 23, 1997 [JP] Japan ................................... 9-105892

[51] Int. Cl.$^7$ ................................................ C07K 14/47
[52] U.S. Cl. .............................................................. 530/350
[58] Field of Search ............................................. 530/350

[56] References Cited

FOREIGN PATENT DOCUMENTS

97/30065  8/1997  WIPO .
97/39105  10/1997  WIPO .

OTHER PUBLICATIONS

Caldwell, Yakubutsu Dotai (Xenobiotic Metabolism and Disposition), vol. 1(1), pp. 119–125 1996.
Ngo et al, The Protein Folding Problem and Tertiary Structure Prediction, Mertz et al (eds.), Birkhauser, Boston, pp. 433 and 492–495, 1994.
Nakao et al, Nature, vol. 389: pp. 631–635, Oct. 9, 1997.
A. Nakao et al., "Identification of Smad2, a Human Mad–related Protein in the Transforming Growth Factor β Signaling Pathway", The Journal of Biological Chemistry, vol. 272, No. 5, pp. 2896–2900, Jan. 1997.
Y. Zhang et al., "The Tumor Suppressor Smad4/DPC4 as a Central Mediator of Smad Function", Current Biology, vol. 7, No. 4, pp. 270–276, Mar. 1997.

*Primary Examiner*—Terry McKelvey
*Attorney, Agent, or Firm*—Wenderoth, Lind & Ponack, L.L.P.

[57] ABSTRACT

A novel signal transduction factor and a gene encoding the same are provided. The present novel signal transduction factor has, for example, the amino acid sequence set forth in SEQ ID NO: 4, and the DNA sequence encoding the factor has, for example, the sequence set forth in SEQ ID NO: 1.

2 Claims, 6 Drawing Sheets

```
Smad7   1:MFRTK----RSALVRRLWRSRAPGGEDEEEGVGGGGGGELRGEGVTDGRAYGAGGGGAGRAGCCLGKAVRGAKGHRHPHPPTSGAGAAG  86
Smad1   1:MNVTSLSFSFTSPAVKRLL---GWKQGDEEEKW--------------------------------------------------------  29
          *  *'  ****

Smad7   87:GAEADLKALTHSVLKKLKERQ-LELLLQAVESRGGTRTACLLLPGRLDCRLGPGAPASAQPAQPPSSYSLPLLLCKVFRWPDLRHSSEVK 175
Smad1   31:-AE---KAV-DALVKKLKKKGAMEELEKALSCPGQPSNCVTIPRSLDGRL---------QVSHRKGLPHV--IYCRVWRWPDLQSHHELK 104
          **    *  *****' '  '' *' **'  * '*'     * *'' ' ' '* ***** * '*

Smad7   176:RLCCCESYGKINPELVCCNPHHLSRLCE----------------------------- 203
Smad1   105:PLECCEFPFGSKQKEVCINPYHYKRVESPVLPPVLVPRHSEYNPQHSLLAQFRNLGQNEPHMPLNATFPDSFQQPNSHPFPHSPNSSYPN 194
          * ***         **' **'*'*'

Smad7   204:-----------------LESPPPPYSRYPMDFLKPTAGCPDAVPSSVETGGTNYLAPGGLSDSQLLLEPGDRSHWCVVAYWE 268
Smad1   195:SPGSSSSTYPHSPTSSDPGSPFQMPADTPPPAYL-PPEDPMT-QDGSQPMDTNMWAPPLPSEINRG---DVQAVA-YEEPKHWCSIVYYE 278
                              '' *****' *  * *'  **  *  *   ** *                      ''*** '  ' ***' ***

Smad7   269:EKTRVGRLYCVQEPS-L-DIFYDLPQG-NGFCLGQLNSDNKSQLVQKVRSKIGGCIQLTREVDGVWVYNRSSYPIFIKSATLD-NPDSRT 354
Smad1   279:LNNRVGEAFHASSTSVLVDGFTDPSNNKNRFCLGLLSNVNRNSTIENTRRHIGKGVHLYYVGGEVYAECLSDSSIFVQSRNCNYHHGFHP 368
          '' *** *      *  '    *' ** **** '  ***'  ** '  *' *  * * *'' ** '   **'    *

Smad7   355:LLVHKVFPGFSIKAF-DYEKAYSLQRPNDHEFMQQ-PWTGF-TVQISFVKGWGQCYTRQFISSCPCWLEVIFNSR---------- 426
Smad1   369:TTVCKIPSGCSLKIFNNQEFAQLLAQSVNHGFETVYELTKMCTIRMSFVKGWGAEYHRQDVTSTPCWIEIHLHGPLQWLDKVLTQMGSPH 458
          * ** *'   *'**      ** *  '  ** *  *    *  *'  ******  * ** '   *****' ' ***'

Smad7   :---------
Smad1   459:NPISSVS 465
```

`*` indicates an amino acid residue common to Smad7 and Smad1.

`'` indicates an amino acid position at which the residue in Smad7 exhibits a similar property to that in Smad1.

Fig. 6

ISOLATED SMAD PROTEIN

BACKGROUND OF THE INVENTION

1. Field of the Invention

The present invention relates to a novel gene encoding a family of proteins, called Smad, which intracellularly transduce stimuli elicited by a physiologically active substance belonging to the transforming growth factor beta (hereinafter referred to as TGFβ) family.

2. Description of the Prior Art

The TGFβ family is a group of peptidic physiologically active substances widely distributed in the animal kingdom. This family include very important physiologically active peptides such as TGFβ found as a substance involved in proliferation of tumor cells, bone morphogenetic protein (BMP) that has a significant function for bone formation in vertebrates including human, inhibin that regulates the secretion of follicle-stimulating hormone from pituitary gland, activin that possesses activity as an erythroide differentiation factor, and neurotrophic factor derived from glial cells (Bock, G. R. and Marsh, J. eds., 1991, Clinical Application TGFβ, Ciba Foundation Symposium, Johns Wiler & Sons). A clue to the solution of the question of how the TGFβ family peptides act on cells was initially obtained by cDNA cloning of receptors for these peptides and by determining their nucleotide sequences together with the amino acid sequences deduced therefrom. Receptors for this family have a transmembrane-type protein-phosphotransferase activity (protein kinase activity) specific to serine (and threonine) residues. This fact demonstrates that phosphorylation of intracellular protein is involved in transduction of stimuli from the TGFβ family (Sporn, M. B. and Roberts, A. B. eds., 1990, "Peptide Growth Factors and Their Receptors", part I and II, Springer-Verlag, Berlin).

As factors mediating stimuli from the TGFβ family, genes designated as Mad and Sma are hitherto known in Drosophila and Nematoda, respectively. In recent years, several genes showing homology to Mad and Sma have been found in several vertebrates including human. Their cDNAs have been cloned and their nucleotide sequences were determined. Those genes and the proteins encoded by the same were named Smad, and to date, Smad1, Smad2, Smad3, Smad4, Smad5, and Smad6 have been reported (Derynck R. et al., 1996, "Nomenclature: Vertebrate mediators of TGFβ family signals", Cell, 18, 173). Furthermore, during early embryogenesis, Smad1 is known essential for a basic and significant determination as for which side of the embryo becomes dorsal and the other becomes ventral (Graff, J. M. et al., 1996, Cell, 85, 479–487). It has been shown that inactivation of Smad2 gene is one of the causes for colorectal cancer in human, while Smad4 gene is shown to be identical to a tumor suppressor gene DPC4 that is known to be strongly associated with repression of pancreatic cancer (Eppert, K., et al., 1996, Cell, 86, 543–552; Hahn, S. A. et al., 1996, Science, 271, 350–353). Thus, the Smad protein family may be signal transduction factors which transduce stimuli from physiologically active peptides of the TGFβ family, while they may also be factors profoundly involved in generation of cancer.

The known Smad family proteins are intracellular proteins consisting of about 400–550 amino acid residues which have an amino- and a carboxy-terminal regions relatively well conserved among the family. As a consequence of increased kinase activity of the specific receptors induced by the TGF β family stimulus, Smad proteins are rapidly phosphorylated and concentrated into nucleus. In the nucleus, the area of gene transcription, Smad proteins uniquely regulate gene expression through unknown mechanism mediated by oligomer formation among the same or different kinds of molecules (Massagu J., 1996, Cell, 85, 947–950).

In recent years, it has been found out that a variety of physiologically active substances like TGFβ, including hormones and cytokines, function eventually through regulation of gene expression in the target cells. Specificity of activity of each physiologically active substance is determined by the nature of receptor and subsequent signal transduction factor for the particular substance. In addition, a signal caused by a single physiologically active substance often activate several kinds of signal transduction factors, which results in branching of the transduction pathway. Isolation of signal transduction factors and elucidation of their properties are therefore helpful to understand mechanisms through which various physiologically active substances function, and to employ the factors as targets for pharmaceuticals.

As described above, the TGFβ family members play very important roles in various physiological events including growth control, immune response, cell differentiation, morphogenesis during embryo and the like. More than 50 physiologically active substances belonging to the TGFβ family are hitherto known, and they include substances of which deficiency or excess in quantity, or abnormality in quality is known to be associated with pathologies related to the above physiological events, such as cancer, autoimmune disease, osteoporosis, anemia, congenital deformity and the like. Similarly, genetic analyses have also shown that defects in the Smad family, which transduces stimuli (signals) from the TGFβ family, is involved in various abnormalities or pathologies, for example, in cancer which is the highest cause of death in advanced countries including many of Europe and North America. For prevention or treatment of cancer, it is desirable to elucidate all of the genes associated with cancer. However, relatively small number of Smads have been hitherto identified when compared with the already known physiologically active substances belonging to the TGFβ family. This fact suggests that there remain unidentified Smad family members. Therefore, isolation of a novel Smad gene will enable us to find a further pathway involving the TGFβ family, and such a gene is expected to be useful as a diagnostic agent for detecting abnormalities, such as tumor, at gene level.

The present invention aims to provide a novel factor belonging to the Smad family which transduces a signal of a physiologically active substance of the TGFβ family, and to provide a gene encoding said factor.

In view of the important role, in biological responses, of TGFβ peptides and their signal transducer Smad family proteins, the present inventors screened cDNAs derived from *Mus musculus* in order to clone a novel Smad gene. As a result, cDNA clones which correspond to mRNA encoding a novel Smad family protein were identified in a cDNA mixture derived from the whole tissue of the 17-day embryos. The present invention has been completed on the basis of this finding.

SUMMARY OF THE INVENTION

Specifically, the first object of the present invention is to provide a gene encoding a novel signal transduction factor which belongs to the Smad family.

The second object of the present invention is to provide a protein encoded by the above gene, that is, a signal transduction factor.

DETAILED DESCRIPTION OF THE INVENTION (1) A gene encoding a signal transduction factor Smad7

The novel Smad in the present invention (Smad7) has the following characteristics.

1) coding region

As shown in SEQ ID NO: 1, it consists of 1281 nucleotide pairs, and encodes a sequence consisting of 426 amino acid residues shown in SEQ ID NO: 4.

2) 5' terminal non-coding region

It comprises 209 nucleotide pairs shown in SEQ ID NO: 2, and the coding region described in 1) is contiguously linked to its 3' end.

3) 3' terminal non-coding region

It comprises 207 nucleotide pairs and is linked immediately to the coding region described in 1).

The cDNA for the novel Smad of the present invention (Smad7) was obtained by the procedures as described below. Firstly, a highly homologous region was determined among the amino acid sequences of vertebrate Smad family members already reported. The amino acid sequence of such highly homologous region is expected to be essential for important function of the Smad family, and therefore, it must be conserved also in unknown Smads. Accordingly, oligonucleotide primers for DNA amplification by PCR (polymerase chain reaction) method were designed and synthesized (Saiki, R. et al., 1985, *Science*, 230, 1350–1354) on the basis of the information about the highly homologous region. A pool of cDNA mixture which was prepared using a publicly known method (Kenji Okazaki, 1995, "mRNA-No-Chousei-Hou", Shunsuke Uda et al. eds., In "Meneki-Jikken-Sousa-Hou", vol I, pp. 349–352, Nankodou) from polyadenylated RNAs derived from *Mus musculus* embryos and which was ligated to an adapter DNA was used as a template source in the PCR. The PCR was performed using the primer oligonucleotide described above in combination with an oligomer specific to the adapter DNA. The partial amino acid sequences deduced from the nucleotide sequence of a PCR product was recognized to have a homology with the amino acid sequence of the Smad family proteins. Based on the nucleotide sequence thus obtained, oligomers corresponding to the 5' and 3' termini were synthesized, and used in the PCR in which the above cDNA mixture was used as a template source to obtain a cDNA containing the entire coding region. After cloning of this cDNA in a general-purpose plasmid vector, the nucleotide sequence was determined. Since the nucleotide sequence of this cDNA is now shown in SEQ ID NOs: 1, 2 and 3, one can also obtain this cDNA by synthesizing sense and antisense oligomers respectively corresponding to the 5'- and 3'-termini of the DNA, and then performing a PCR in which a *Mus musculus* embryo cDNA mixture is used as a template source.

When the amino acid sequence deduced from the cDNA sequence so obtained was compared with the known amino acid sequence of Smad1 (NCBI (U.S. National Center for Biotechnology Information) Identification numbers: 1332714, 1333647, 1381671, 1518645, and 1654323), it was revealed that the sequences exhibit relatively high homology of 65% in the C-terminal region, demonstrating that the obtained cDNA encodes a Smad family protein. In addition, the amino acid sequence is apparently different from the sequence of any one of the previously disclosed vertebrate-derived Smad family members, Smad1–Smad6 (NCBI Identification: Smad1; 1518645, 1658159, 1333647, 1654323, 1469308, 1438077, 1332714: Smad2; 1407782, 1575530: Smad3; 1673577, 1552532: Smad4; 1724091, 1163234: Smad5; 1518647, 1654325: Smad6; 1654327) and from the invertebrate-derived Drosophila Mad (NCBI Identification: 1085150, 551489) and Nematoda Sma (NCBI Identification: 1173452, 1173453, 1173454). Thus, the present cDNA was identified as cDNA for a novel Smad family protein and designated as Smad7. The nucleotide sequence of the present cDNA is also distinctly different from any one of previously disclosed Smad family cDNAs (GenBank accession numbers: Smad1; U54826, U57456, U58992, U59912, U59423, U58834, L77888: Smad2; U59911, U60530, U65019, U68018, L77885: Smad3; U68019, U76622: Smad4; U79748, U44378: Smad5; U58993: Smad6; U59914).

(2) Smad7 Protein

The Smad7 protein of the present invention has the following characteristics.

1) Amino acid sequence

The amino acid sequence deduced from the above Smad7 cDNA nucleotide sequence is shown in SEQ ID NO: 4.

2) Molecular weight

The molecular weight of Smad7 protein calculated from the amino acid sequence shown in SEQ ID NO: 4 is 46516.

3) Isoelectric point

The isoelectric point of Smad7 protein calculated from the amino acid sequence shown in SEQ ID NO: 4 is 8.3.

Smad7 protein was obtained by the procedures as described below.

Smad7 cDNA shown in SEQ ID NO: 1 was ligated downstream to a promoter region in a known expression plasmid vector, and the vector was transformed into *E. coli* cells, from which the plasmid DNA was then purified. The plasmid DNA was then introduced into cultured cells to produce Smad7 protein. As a vector for the expression of Smad7, pactEF-mSmad7 (FIG. 1) constructed by the present inventors was used. *E. coli* strain transformed with this vector, *Escherichia coli* (pactEF-mSmad7), has been deposited with National Institute of Bioscience and Human Technology (deposition date: Apr. 8, 1997; accession number: FERM P-16187). Smad7 protein can be synthesized in *E. coli* cells transformed with Smad7 cDNA. There are many known vectors for expression in *E. coli* cells, and one can construct a desirable expression vector by inserting Smad7 cDNA into one of those known vectors. Such known vectors are, for example, pET series vectors, pKC30, and the like (Sambrook, J. et al., 1989, "Molecular Cloning", Cold Spring Harbor Laboratory Press, USA).

In addition, a fusion protein in which the entire or a part of Smad7 protein is fused to another amino acid sequence can also be expressed. To this end, a gene or oligonucleotide encoding an amino acid sequence to be added is ligated to the entire or a part of Smad7 cDNA so that the codon frames for both sequences agree with each other.

Furthermore, the Smad7 cDNA shown in SEQ ID NO: 1 may be transcribed into RNA, and the RNA so obtained may be added to an intracellular translation system or cell-free translation system to synthesize Smad7 protein. There are many known vectors for transcription of cloned DNA into RNA. For example, SP64, pIBI31, pGEM3 and the like may be used for this purpose (Sambrook, J. et al., 1989, "Molecular Cloning", Cold Spring Harbor Laboratory Press, USA). As RNA polymerases, those derived from bacteriophages SP6, T3 and T7 may be used. As a system for synthesizing protein from synthesized sense-strand RNA, a system using oocytes of *Xenopus laevis* is known (Mayumi Nishizawa, Noriyuki Sakata, 1992, "in vitro-No-Tanpakushitu-No-Seigousei", In "Shin-Seikagaku-Jikken-Kouza, 1, Tanpakushitu VI", edited by The Japanese Biochemical Society, Tokyo Kagaku Dojin). Similarly, a method using rabbit reticulocyte lysate may also be used as a cell-free translation system (Kozak, M., 1990, *Nuc. Acids Res.*, 18, 2828). In another embodiment, the Smad7 cDNA shown in SEQ ID NOs: 1, 2 and 3 or a part thereof may be used as a template to synthesize an antisense RNA for Smad7. Such antisense RNA may be used for diagnosis of Smad7-related pathologies. Furthermore, by ligating DNA having an appropriate sequence to a transcription vector containing a sequence for Smad7, antisense RNA may be synthesized as RNA molecule having a ribozyme activity.

According to known techniques, one skilled in the art can obtain mutant proteins in which deletion, substitution or insertion of one or more amino acid residues are introduced into the amino acid sequence shown in SEQ ID NO: 4, by introducing mutation(s) into the DNA shown in SEQ ID NO: 1 in the Sequence Listing, for example, by a site-directed mutagenesis. Among such mutant proteins, those retaining a signal transduction activity are included within the scope of the present invention.

EXAMPLES

The present invention is further illustrated by the following Examples.

Example 1

Cloning of *Mus musculus* Smad7 cDNA

1) Design of primer oligonucleotide and PCR

A gene-specific antisense oligomer GSP1 (Gene Specific Primer 1) having a sequence:

GTT(A/C/G/T)A(A/G)GTG(A/C/G/T)AC(C/T)TC(A/C/G/T)-
A(G/T)CCAGCA(A/C/G/T)GG-3' (SEQ ID NO:5)

was synthesized on the basis of the following amino acid sequence:

Pro Cys Trp Leu/Ile Glu Val/Ile His Leu Asn (SEQ ID NO: 6)

which is well conserved among Smad proteins. Similarly, another gene-specific antisense oligomer GSP2 having a sequence:

(SEQ ID NO:7)
5'-GTA(A/C/G/T)(C/T)(A/C)(A/C/G/T)G(C/G)(A/C/G/T)-
CCCCA(A/C/G/T)CC(C/T)TT(A/C/G/T)AC(A/G)AA-3' was synthesized on the basis of the following amino acid sequence:

(SEQ ID NO:8)
Phe Val Lys Gly Trp Gly Ala/Pro/Cys/Glu Thr.

The first PCR was performed using adapter oligonucleotide-attached cDNA mixture derived from *Mus musculus* 17-day embryo (manufactured by CLONTECH, USA) as a template pool, with the following adapter-specific oligomer 1:

(SEQ ID NO:9)
(AP1) 5'-CCATCCTAATACGACTCACTATAGGGC-3' as a sense oligomer and the above GSP1 as an antisense oligomer. The reaction conditions were as follows: after 180 seconds at 96° C., 5 cycles of denaturation at 96° C. for 30 seconds and annealing/elongation at 72° C. for 240 seconds, 5 cycles of denaturation at 96° C. for 30 seconds and annealing/elongation at 70° C. for 240 seconds, and then 25 cycles of denaturation at 96° C. for 30 seconds, annealing at 60° C. for 30 seconds and elongation at 68° C. for 120 seconds.

Then, DNA molecules contained in 1/500 volume of the reaction mixture so obtained was used as templates in the second PCR in which the following adapter-specific oligomer 2:

(AP2): 5'-ACTCACTATAGGGCTCGAGCGGC-3' (SEQ ID NO:10)

and the above GSP2 were used as sense and antisense oligomers, respectively. The reaction conditions were as follows: after 2 minutes at 96° C., 20 cycles of denaturation at 96° C. for 30 seconds and annealing/elongation at 68° C. for 120 seconds. In these PCR, Expand High Fidelity PCR System (BOEHRINGER MANNHEIM, Germany) (Barnes, W. M., 1994, *Proc. Natl. Acad. Sci. USA*, 91, 2216–2220) was used as thermostable DNA polymerase, and PCR Thermal Cycler MP (TAKARA SHUZO) was used as a heat cycle equipment.

Analysis of the nucleotide sequence of about 1,200 bp DNA fragment obtained in the above PCR revealed that it contained both sequences encoding the following two amino acid sequences conserved among the Smad family, Lys Lys Leu Lys Glu (SEQ ID NO:11), and
Arg Trp Pro Asp Leu (SEQ ID NO:12).

The DNA fragment was, therefore, considered to be derived from cDNA encoding a Smad family protein.

2) Analysis of the 5' and 3' terminal regions

On the basis of the nucleotide sequence obtained in the above item 1), the following Smad-specific antisense oligomer:

5'-CCGGACGAGCGCAGATCGTTTGGTCC-3' (SEQ ID NO:13)

was synthesized in order to perform a 5'-RACE (rapid amplification of 5'-cDNA ends) (Frohman, M. A., 1993, *Methods. Enzymol.*, 218, 340–358). Similarly, the following Smad-specific sense oligomer:

5'-TTCATGCAGCAACCATGGACGGGTTTC-3' (SEQ ID NO:14)

was also synthesized in order to perform a 3'-RACE (rapid amplification of 3'-cDNA ends) (Frohman, M. A., 1993, *Methods. Enzymol.*, 218, 340–358). In these reactions, the same cDNA mixture derived from *Mus musculus* 17-day embryos as that used in the above item 1) was used as template source, together with AP2 and the Smad-specific antisense oligomer for 5'-RACE, or together with the Smad-specific sense oligomer and AP2 for 3'-RACE. The reaction conditions were as follows: after 180 seconds at 96° C., 5 cycles of denaturation at 96° C. for 30 seconds and annealing/elongation at 72° C. for 240 seconds, 5 cycles of denaturation at 96° C. for 30 seconds and annealing/elongation at 70° C. for 240 seconds, and then 25 cycles of denaturation at 96° C. for 30 seconds, annealing at 60° C. for 30 seconds and elongation at 68° C. for 240 seconds.

Nucleotide sequencing of about 250 bp DNA fragment obtained in this 5'-RACE revealed that it contains an initiation codon located at the position conserved among the Smad family and the 5' non-coding region shown in SEQ ID NO: 2. Similarly, nucleotide sequencing of about 400 bp DNA fragment obtained in the above 3'-RACE revealed that it contains an termination codon and the 3' non-coding region shown in SEQ ID NO: 3.

3) Cloning of Smad7 coding region

On the basis of the nucleotide sequence determined in the above item 2), the following specific sense oligomer (to which an NheI site for cloning has been added at the 5'-end):

```
23 (SEQ ID NO:15)
5'-CCGCTAGCACCATGTTCAGGACCAAACGATCTGCGCTCGTC-3'
``` and the following antisense oligomer (to which a BamHI site for cloning has been added at the 5'-end):

```
                                          (SEQ ID No: 16)
5'-CCGGATCCTATCGCGAGTTGAAGATGACCTCCAGCCAGCACG-3'
``` were prepared. With these two oligomers, PCR was performed using the same cDNA mixture as that described in the above item 1) as template source. The reaction conditions were as follows: after 180 seconds at 96° C., 5 cycles of denaturation at 96° C. for 30 seconds and annealing/elongation at 72° C. for 60 seconds, 5 cycles of denaturation at 96° C. for 30 seconds and annealing/elongation at 70° C. for 60 seconds, and then 25 cycles of denaturation at 96° C. for 30 seconds, annealing/elongation at 68° C. for 60 seconds.

About 0.5 μg of about 1,300 bp DNA fragment obtained in the above reaction was treated with restriction enzymes NheI (New England Biolabs, USA) and BamHI (New England Biolabs, USA) at 37° C. for one hour, and then purified by gel electrophoresis in 0.7% low-melting point agarose. The DNA fragment was then cloned using a known plasmid vector pIBIΔ (International Biotechnologies, Inc., USA; it may be prepared from pIBI31 according to the method of Furuno, N. et al., 1994, *EMBO J.*, 13, 2399–2410) and host cells, JM109, derived from *E. coli* K-12 strain (Sambrook, J. et al., 1989, "Molecular Coning", Cold Spring Harbor Laboratory Press, USA) (TOYOBO, Japan) to obtain a plasmid pIBIΔ-mSmad7 (FIG. 3). *E. coli* strain transformed with this plasmid, *Escherichia coli* (pIBIΔ-mSmad7) has been deposited at National Institute of Bioscience and Human Technology (deposition date: Apr. 8, 1997; accession number: FERM P-16188). The deposition was converted to the international deposition under Budapest Treaty on Mar. 30, 1998, and assigned new accession number FERM BP-6317. This plasmid DNA was then isolated, and the nucleotide sequence of the cDNA was determined. The nucleotide sequence is shown in SEQ ID NO: 1. Furthermore, Smad7 cDNA having the sequence shown in SEQ ID NO: 1 was also obtained from *Mus musculus* 11-day embryos using the identical procedures.

Example 2

Construction of Smad7 Expression Vector

Figure 1:
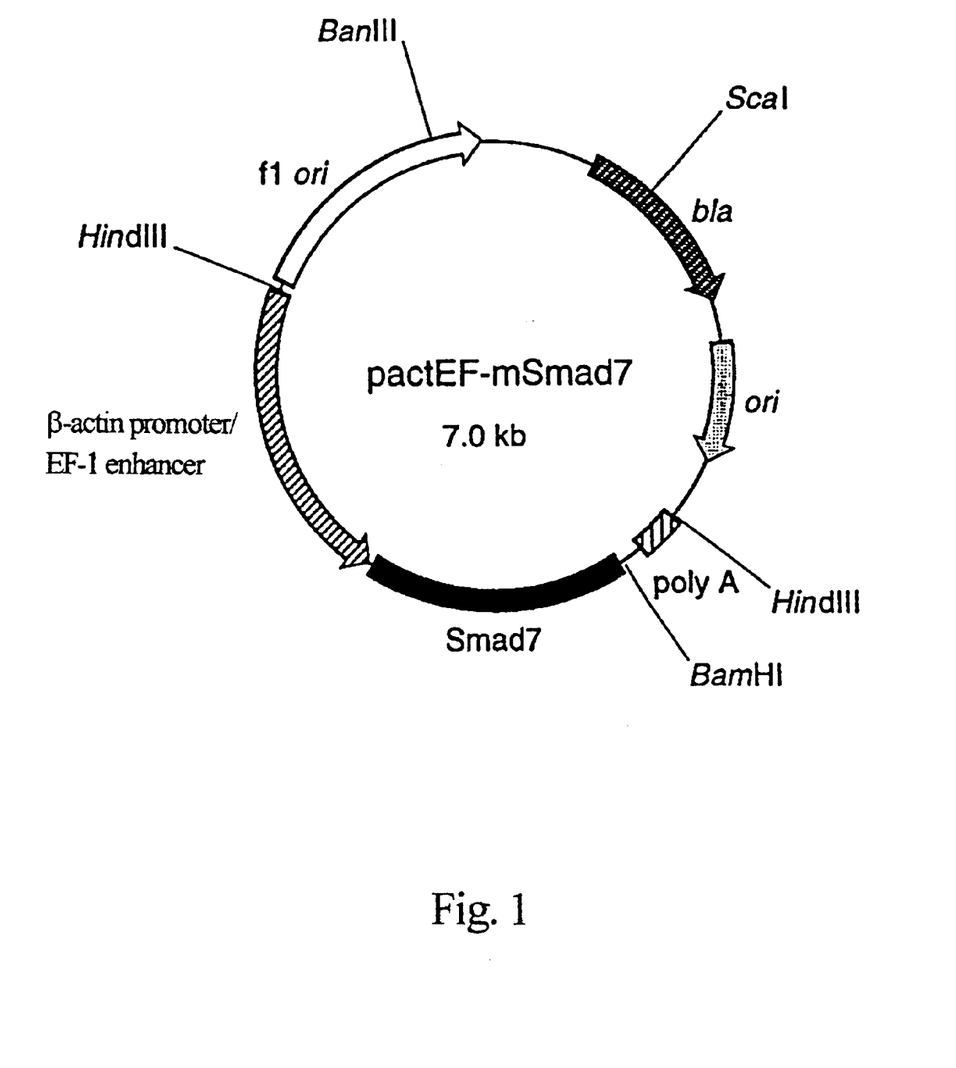
FIG. 1 is a gene map of an expression vector pactEF-Smad7 for expression of Smad7 in animal cells.

The Smad7 cDNA obtained above, which contains the entire coding region, was inserted into an expression vector for cultured animal cells, pactEF (BOEHRINGER MANNHEIM, Germany; it may be prepared from pEMBL9 (+) according to the method of Okazaki K. and Sagata, N., 1995, *EMBO J.*, 14, 5048–5059), to construct pactEF-mSmad7 (FIG. 1). As above, *E. coli* strain transformed with this vector, *Escherichia coli* (pactEF-mSmad7), has been deposited with National Institute of Bioscience and Human Technology (deposition date: Apr. 8, 1997; accession number: FERM P-16187). The deposition was converted to the international deposition under Budapest Treaty on Mar. 30, 1998, and assigned new accession number FERM BP-6316. In FIG. 1, β-Actin promoter/EF-1α enhancer means a transcription promoter of beta-actin derived from chicken genome and the elongation factor 1 alpha derived from human genome; f1 ori means the DNA replication initiating region of f1 phage; bla means a beta-lactamase gene (conferring sulbenicillin resistance and ampicillin resistance); ori means the DNA replication initiating region derived from pUC plasmid; poly A means transcription termination and polyadenylation signal derived from SV40; Smad7 means Smad7 cDNA; HindIII, BanIII, ScaI, and BamHI are the sites at which the DNA is cleaved by respective restriction enzymes.

Figure 2:
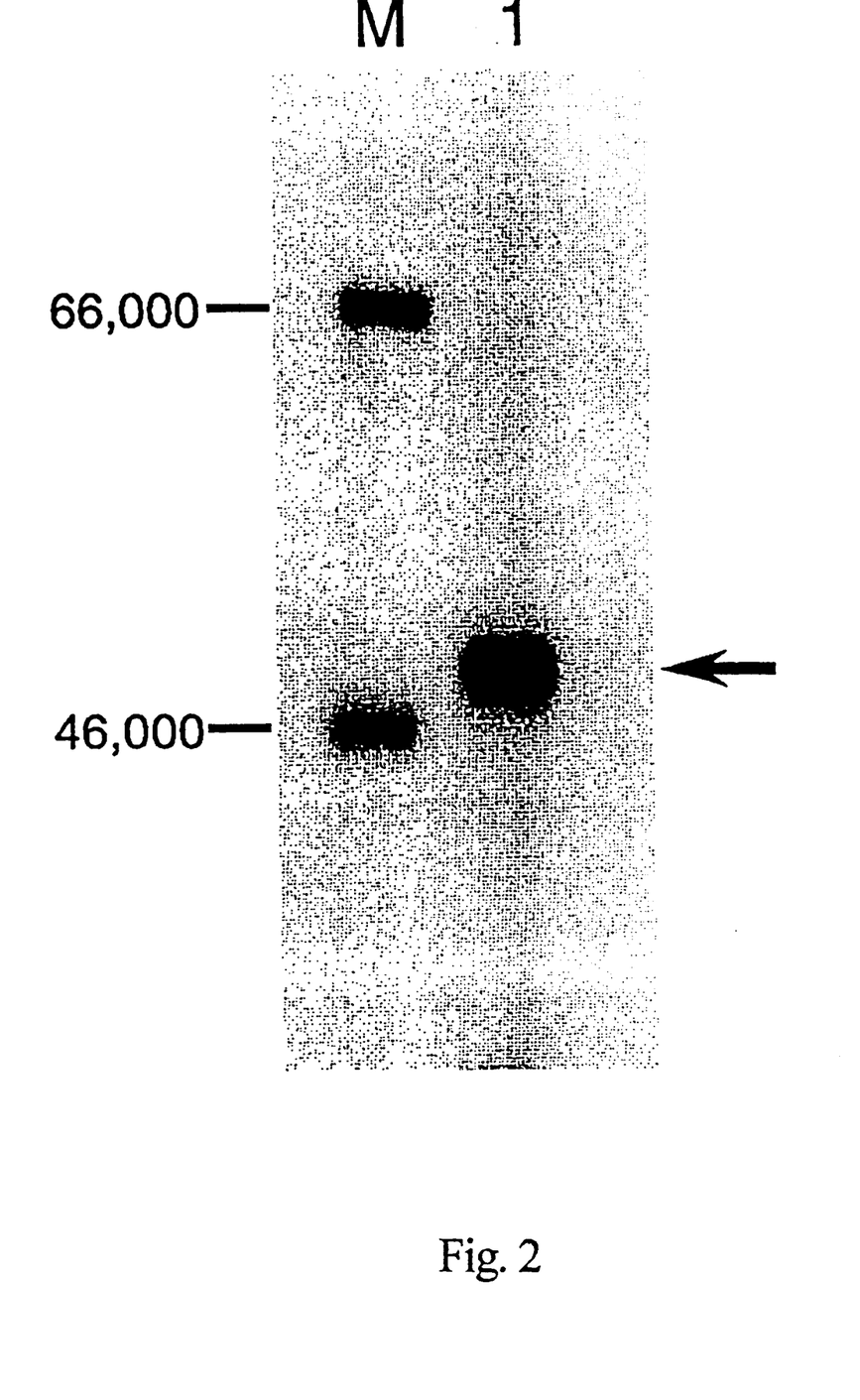
FIG. 2 shows the result of denaturing polyacrylamide gel electrophoresis of a fused protein between Smad7 and Myc-tag peptide.

In addition, a vector pactEF-Myc-mSmad7 was also prepared for expression of the fusion protein in which a fragment containing the following sequence of a known epitope peptide, Myc-tag (Evan, G. I. et al., 1985, *Mol. Cell. Biol.* 5, 3610–3616):

```
                                          (SEQ ID No: 17)
Glu Gln Lys Leu Ile Ser Glu Glu Asp Leu
``` has been added to the N-terminus of Smad7. *E. coli* strain transformed with this vector, *Escherichia coli* (pactEF-Myc-mSmad7), has been deposited with National Institute of Bioscience and Human Technology (deposition date: Apr. 8, 1997; accession number: FERM P-16186). The deposition was converted to the international deposition under Budapest Treaty on Mar. 30, 1998, and assigned new accession number FERM BP-6315. To prepare this vector, the following DNA oligomer:

```
                                          (SEQ ID No: 18)
5'-ATGTCTGAGCAGAAGCTGATCTCTGAG-
GAAGACCTTGGAGCTAGCACC-3'
``` was inserted just before the translation initiation codon of Smad7. This vector DNA was then introduced into mouse NIH3T3 cells by the calcium phosphate method (Graham, F. L. and van der Eb, A. J., 1973, *Virology*, 52, 456–457). After 48 hours, the whole cell extract was separated by denaturing polyacrylamide gel electrophoresis (Laemmli, U. K. et al., 1970, *J. Mol. Biol.*, 49, 99–113), and analyzed by immunoblotting (Harlow, E. and Lane D., 1988, "Antibodies", Cold Spring Harbor Laboratory Press, USA) using anti-Myc-tag monoclonal antibody (SANTA CRUZ, USA). The electrophoretic analysis revealed expression of the fused protein between Smad7 and Myc-tag as a band at the position corresponding to a molecular weight of about 48,000 (FIG.

2). In FIG. 2, Lane M shows molecular weight markers; Lane 1 shows the fused protein between Smad7 and Myc-tag peptide synthesized in animal cells.

Example 3

Synthesis of Smad7 RNA

Figure 3:
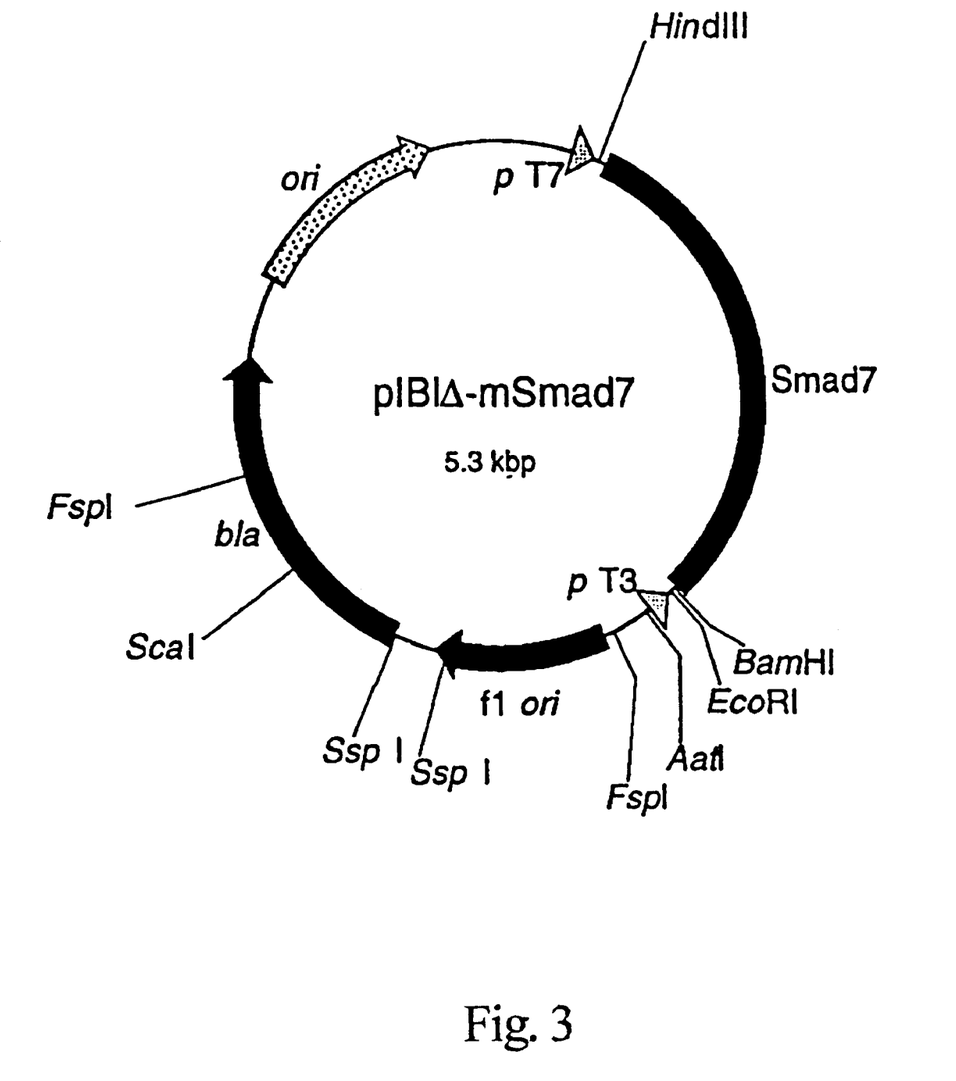
FIG. 3 is a gene map of a plasmid vector pIBIΔ-mSmad7 in which Smad7 has been cloned.
Figure 4:
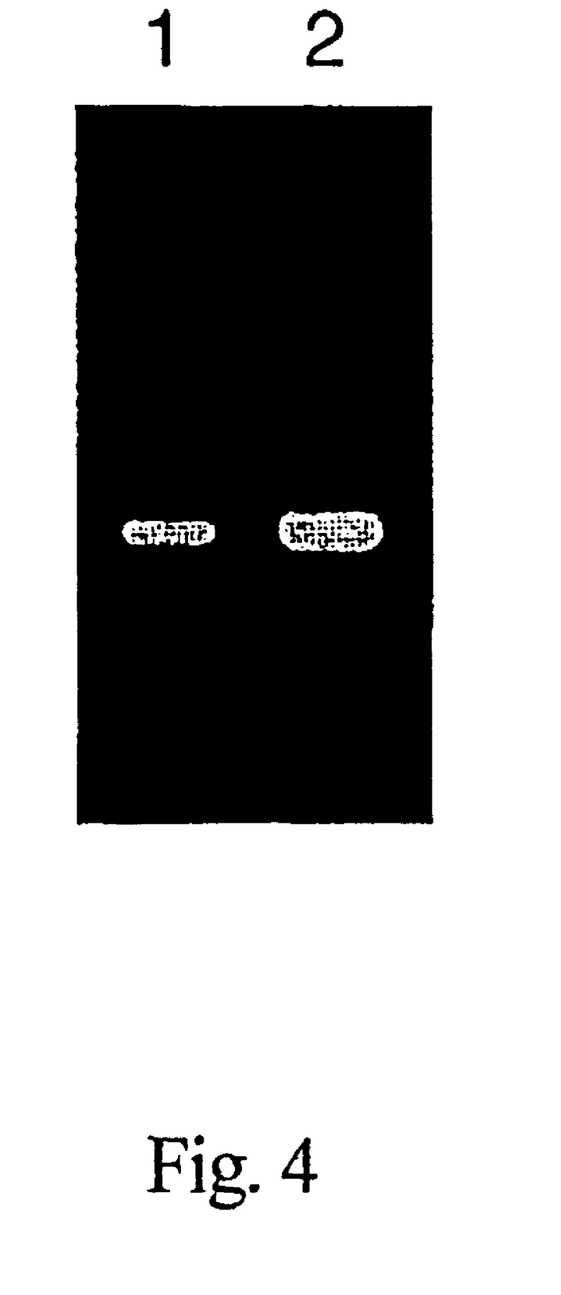
FIG. 4 shows the result of agarose gel electrophoresis of mRNA (sense-strand RNA) and antisense RNA for Smad7.

The vector pIBIΔ into which the Smad cDNA was cloned in Example 1 contains a promoter sequence for phage T7 RNA polymerase upstream to the cDNA, and also a promoter sequence for phage T3 RNA polymerase downstream to the cDNA (Furuno, N. et al., 1994, *EMBO J.*, 13, 2399–2410). Therefore, in order to obtain a sense-strand RNA of Smad7, 2 μg of the plasmid pIBIΔ-mSmad7 (FIG. 3) described in Example 1, which was obtained by cloning Smad7 cDNA into pIBIΔ, was treated with restriction enzyme BamHI at 37° C. for one hour, and the linearized plasmid so obtained was then subjected to a transcription step using T7 RNA polymerase (Ambion, USA). The synthesized RNA was gel-electrophoretically homogeneous (FIG. 4). Similarly, 2 μg of the above cDNA was treated with restriction enzyme HindIII at 37° C. for one hour, and the linearized plasmid so obtained was then subjected to a transcription step using T3 RNA polymerase (Ambion, USA). The synthesized antisense RNA was gel-electrophoretically homogeneous (FIG. 4). In FIG. 3, f1 ori means the DNA replication initiating region of f1 phage; bla means a beta-lactamase gene (conferring sulbenicillin resistance and ampicillin resistance); ori means the DNA replication origin region derived from a pUC plasmid; pT7 means a promoter sequence for phage T7 RNA polymerase; Smad7 means Smad7 cDNA; pT3 means a promoter sequence for phage T3 RNA polymerase; FspI, SspI, ScaI, HindIII, BamHI, EcoRI and AatI are the sites at which the DNA is cleaved by respective restriction enzymes. In FIG. 4, Lane 1 shows Smad7 mRNA (sense-strand RNA), and Lane 2 shows Smad7 antisense RNA.

Example 4

Synthesis of Smad7 Protein

Figure 5:
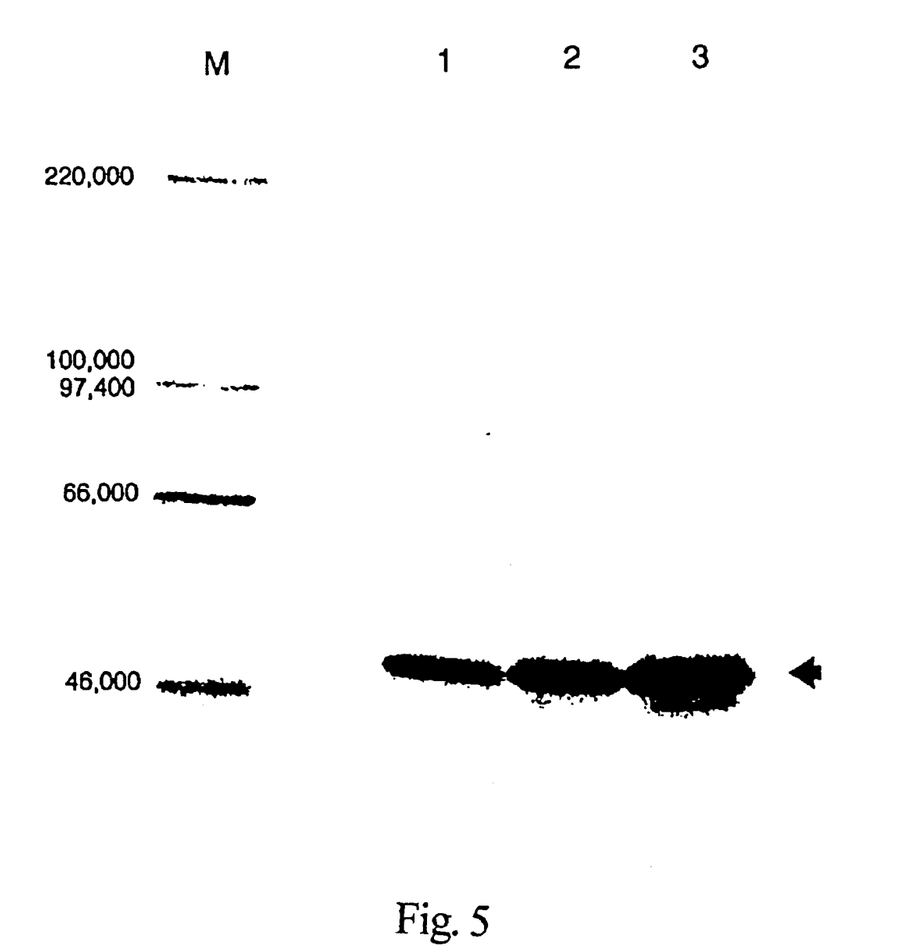
FIG. 5 shows the result of denaturing polyacrylamide gel electrophoresis of Smad7 protein synthesized in vitro.

About 1 μg of the Smad7 sense-strand RNA obtained in Example 3 was added to a cell-free lysate derived from rabbit reticulocytes (Promega, USA) together with $^{35}$S-labeled amino acids (Amersham, UK), and the mixture was subjected to translation at 30° C. for one hour to obtain Smad7 protein. Denaturing polyacrylamide gel electrophoresis of the product along with molecular weight markers revealed that the synthesized Smad7 was a homogeneous protein having molecular weight of about 47,000 (FIG. 5). In FIG. 5, Lane M shows molecular weight markers; Lane 1 shows the Smad7 protein; Lane 2 shows 2-fold amounts of the Smad7 protein as compared with Lane 1; Lane 3 shows 4-fold amounts of the Smad7 protein as compared with Lane 1; and the arrowhead indicates the position of the Smad7 protein.

Figure 6:
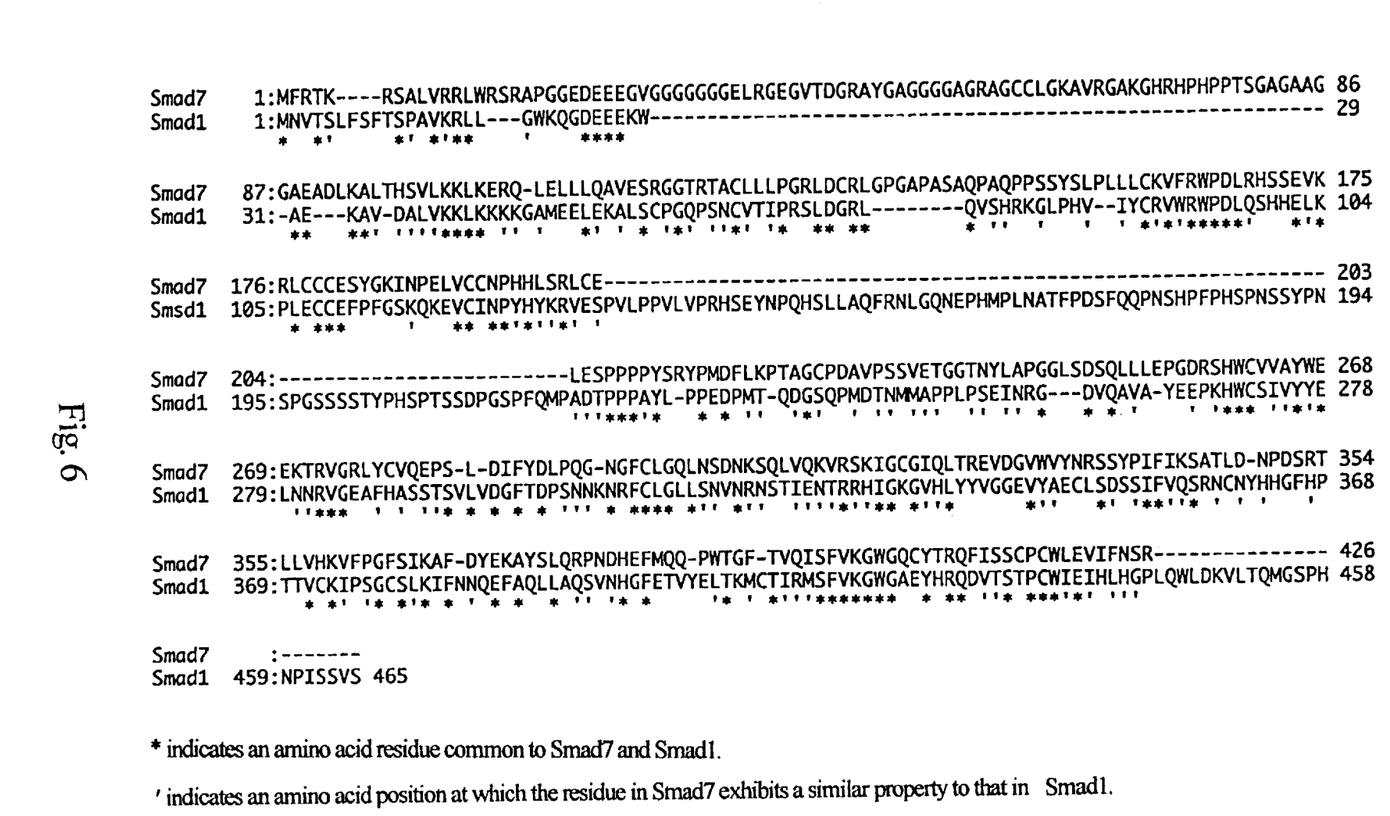
FIG. 6 shows a sequence comparison between Smad7 (SEQ ID NO: 4 ) and Smad1 (SEQ ID NO: 19).

As shown in FIG. 6, the amino acid sequence of the novel factor of the present invention, Smad7, contains a region highly homologous to the previously known signal transduction factor Smad1. The highly homologous region is also well conserved in other Smad family proteins, suggesting that it is a region essential for the Smad activity. It is, therefore, believed that Smad7 having this region retains the function as a signal transduction factor.

Example 5

Using the Smad7 protein as antigen, which was prepared from the expression vector obtained by the procedures described above, antisera specific to Smad7 protein may be obtained by immunizing rabbits according to a known method (Harlow, E. and Lane D., 1988, "Antibodies", Cold Spring Harbor Laboratory Press, USA). The antisera so obtained may be further affinity-purified by using Smad7 protein as affinity ligand according to a known procedure (Harlow, E. and Lane D., 1988, "Antibodies", Cold Spring Harbor Laboratory Press, USA) to obtain inhibitory antibody highly specific to Smad7 protein. This inhibitory antibody may be added to a reaction mixture in order to assay the activity of Smad7. Furthermore, this inhibitory antibody may be micro-injected into living cells by a known method (Capecchi, M., 1980, *Cell*, 22, 479–488) in order to confirm the signal transduction activity in the cells. Similarly, the vector pactEF-mSmad7 DNA described above (FIG. 1) may also be directly injected into cells in order to assay the activity of the expressed product, i.e. Smad7 protein.

Thus, the novel signal transduction factor of the present invention and the gene encoding the same are useful as a pharmaceutical or diagnostic agent.

---

What we claim is:

1. An isolated protein having a signal transduction activity which comprises the amino acid sequence shown in SEQ ID NO: 4.

2. A composition comprising the protein of claim 1 and a carrier.

* * * * *

SEQUENCE LISTING (1) GENERAL INFORMATION:

(iii) NUMBER OF SEQUENCES: 19

(2) INFORMATION FOR SEQ ID NO:1:

(i) SEQUENCE CHARACTERISTICS:
      (A) LENGTH: 1281 bases
      (B) TYPE: nucleic acid
      (C) STRANDEDNESS: double
      (D) TOPOLOGY: linear    (ii) MOLECULE TYPE: cDNA    (vi) ORIGINAL SOURCE:
      (A) ORGANISM: Mus musculus
      (B) STRAIN: Swiss-Webster/NIH (xi) SEQUENCE DESCRIPTION: SEQ ID NO:1:

```
ATGTTCAGGA CCAAACGATC TGCGCTCGTC CGGCGTCTCT GGAGGAGCCG TGCGCCCGGC      60

GGCGAGGACG AGGAGGAGGG CGTGGGGGGT GGCGGCGGAG GAGGCGAGCT GCGGGGAGAA     120

GGGGCGACGG ACGGCCGGGC TTATGGGGCT GGTGGCGGCG GTGCGGGCAG GGCTGGCTGC     180

TGCCTGGGCA AGGCAGTCCG AGGTGCCAAA GGTCACCACC ATCCCCATCC CCCAACCTCG     240

GGTGCCGGGG CGGCCGGGGG CGCCGAGGCG GATCTGAAGG CGCTCACGCA CTCGGTGCTC     300

AAGAAACTCA AGGAGCGGCA GCTGGAGCTG CTGCTTCAGG CCGTGGAGTC CCGCGGCGGT     360

ACGCGCACCG CGTGCCTCCT GCTGCCCGGC CGCCTGGACT GCAGGCTGGG CCCGGGGGCG     420

CCCGCCAGCG CGCAGCCCGC GCAGCCGCCC TCGTCCTACT CGCTCCCCCT CCTGCTGTGC     480

AAAGTGTTCA GGTGGCCGGA TCTCAGGCAT TCCTCGGAAG TCAAGAGGCT GTGTTGCTGT     540

GAATCTTACG GAAGATCAA CCCCGAGCTG GTGTGCTGCA ACCCCCATCA CCTTAGTCGA      600

CTCTGTGAAC TAGAGTCTCC CCCTCCTCCT TACTCCAGAT ACCCAATGGA TTTTCTCAAA     660

CCAACTGCAG GCTGTCCAGA TGCTGTACCT TCCTCCGCGG AAACCGGGGG AACGAATTAT     720

CTGGCCCCTG GGGGCTTTC AGATTCCCAA CTTCTTCTGG AGCCTGGGGA TCGGTCACAC      780

TGGTGCGTGG TGGCATACTG GGAGGAGAAG ACTCGCGTGG GGAGGCTCTA CTGTGTCCAA     840

GAGCCCTCCC TGGATATCTT CTATGATCTA CCTCAGGGGA ATGGCTTTTG CCTCGGACAG     900

CTCAATTCGG ACAACAAGAG TCAGCTGGTA CAGAAAGTGC GGAGCAAGAT CGGCTGTGGC     960

ATCCAGCTGA CGCGGGAAGT GGATGGCGTG TGGGTTTACA ACCGCAGCAG TTACCCCATC    1020

TTCATCAAGT CCGCCACACT GGACAACCCG GACTCCAGGA CGCTGTTGGT GCACAAAGTG    1080

TTCCCTGGTT TCTCCATCAA GGCTTTTGAC TATGAGAAAG CCTACAGCCT GCAGCGGCCC    1140

AATGACCACG AGTTCATGCA GCAACCATGG ACGGGTTTCA CCGTGCAGAT CAGCTTTGTG    1200

AAGGGCTGGG GCCAGTGCTA CACCCGCCAG TTCATCAGCA GCTGCCCGTG CTGGCTGGAG    1260

GTCATCTTCA ACAGCCGGTA G                                             1281
```

(2) INFORMATION FOR SEQ ID NO:2:

(i) SEQUENCE CHARACTERISTICS:
        (A) LENGTH: 209 bases
        (B) TYPE: nucleic acid
        (C) STRANDEDNESS: double
        (D) TOPOLOGY: linear     (ii) MOLECULE TYPE: cDNA     (vi) ORIGINAL SOURCE:
        (A) ORGANISM: Mus musculus
        (B) STRAIN: Swiss-Webster/NIH     (xi) SEQUENCE DESCRIPTION: SEQ ID NO:2:

```
CGGCGCCCGC GCGCGCCCCG GCCTCTGGGA GACTGGCGCA TGCCACGGAG CGCCCCTCGG      60

GCCGCCGCCG CTTCTGCCCG GGCCCCTGCT GTTGCTGCTG TCGCCTGCGC CTGCTGCCCC     120

AACTCGGCGC CCGACTTCTT CATGGTGTGC GGAGGTCATG TTCGCTCCTT AGCCGGCAAA     180

CGACTTTTCT CCTCGCCTCC TCGCCCCGC                                      209
```

(2) INFORMATION FOR SEQ ID NO:3:

(i) SEQUENCE CHARACTERISTICS:
        (A) LENGTH: 207 bases
        (B) TYPE: nucleic acid
        (C) STRANDEDNESS: double
        (D) TOPOLOGY: linear (ii) MOLECULE TYPE: cDNA (vi) ORIGINAL SOURCE:
                 (A) ORGANISM: Mus musculus
                 (B) STRAIN: Swiss-Webster/NIH (xi) SEQUENCE DESCRIPTION: SEQ ID NO:3:

TCGGTCGTGT GGTGGGGAGA AGAGGACAGG GCGGATCGTG AGCCGAGCAG GCCCCCGTTC      60

AAACTACTTG CTGCTAACCT TTCCCGAGTG ATTGCTTTTC ATGCAAACTC TTTGGTTGGT     120

GTTGTTATTG CCATTCATTG TTGGTTTTGT TTTGTTCTGT TCTGGTTTGT TTTTTTTTTT     180

TTTTTCCTCC TCCTTTCTCG TTAAAAA                                        207

(2) INFORMATION FOR SEQ ID NO:4:

(i) SEQUENCE CHARACTERISTICS:
                 (A) LENGTH: 426 amino acids
                 (B) TYPE: amino acid
                 (C) STRANDEDNESS: single
                 (D) TOPOLOGY: linear (ii) MOLECULE TYPE: protein (vi) ORIGINAL SOURCE:
                 (A) ORGANISM: Mus musculus
                 (B) STRAIN: Swiss-Webster/NIH (xi) SEQUENCE DESCRIPTION: SEQ ID NO:4:

Met Phe Arg Thr Lys Arg Ser Ala Leu Val Arg Arg Leu Trp Arg Ser
                 5                  10                  15

Arg Ala Pro Gly Gly Glu Asp Glu Glu Gly Val Gly Gly Gly
             20                  25                  30

Gly Gly Gly Glu Leu Arg Gly Glu Gly Ala Thr Asp Gly Arg Ala Tyr
             35                  40                  45

Gly Ala Gly Gly Gly Ala Gly Arg Ala Gly Cys Cys Leu Gly Lys
         50                  55                  60

Ala Val Arg Gly Ala Lys Gly His His His Pro His Pro Pro Thr Ser
65                  70                  75                  80

Gly Ala Gly Ala Ala Gly Gly Ala Glu Ala Asp Leu Lys Ala Leu Thr
                 85                  90                  95

His Ser Val Leu Lys Lys Leu Lys Glu Arg Gln Leu Glu Leu Leu
                100                 105                 110

Gln Ala Val Glu Ser Arg Gly Gly Thr Arg Thr Ala Cys Leu Leu Leu
             115                 120                 125

Pro Gly Arg Leu Asp Cys Arg Leu Gly Pro Gly Ala Pro Ala Ser Ala
         130                 135                 140

Gln Pro Ala Gln Pro Pro Ser Ser Tyr Ser Leu Pro Leu Leu Leu Cys
145                 150                 155                 160

Lys Val Phe Arg Trp Pro Asp Leu Arg His Ser Ser Glu Val Lys Arg
                 165                 170                 175

Leu Cys Cys Cys Glu Ser Tyr Gly Lys Ile Asn Pro Glu Leu Val Cys
             180                 185                 190

Cys Asn Pro His His Leu Ser Arg Leu Cys Glu Leu Glu Ser Pro Pro
         195                 200                 205

Pro Pro Tyr Ser Arg Tyr Pro Met Asp Phe Leu Lys Pro Thr Ala Gly
     210                 215                 220

Cys Pro Asp Ala Val Pro Ser Ser Ala Glu Thr Gly Gly Thr Asn Tyr
225                 230                 235                 240

```
Leu Ala Pro Gly Gly Leu Ser Asp Ser Gln Leu Leu Glu Pro Gly
                245                 250                 255

Asp Arg Ser His Trp Cys Val Val Ala Tyr Trp Glu Glu Lys Thr Arg
            260                 265                 270

Val Gly Arg Leu Tyr Cys Val Gln Glu Pro Ser Leu Asp Ile Phe Tyr
        275                 280                 285

Asp Leu Pro Gln Gly Asn Gly Phe Cys Leu Gly Gln Leu Asn Ser Asp
    290                 295                 300

Asn Lys Ser Gln Leu Val Gln Lys Val Arg Ser Lys Ile Gly Cys Gly
305                 310                 315                 320

Ile Gln Leu Thr Arg Glu Val Asp Gly Val Trp Val Tyr Asn Arg Ser
                325                 330                 335

Ser Tyr Pro Ile Phe Ile Lys Ser Ala Thr Leu Asp Asn Pro Asp Ser
                340                 345                 350

Arg Thr Leu Leu Val His Lys Val Phe Pro Gly Phe Ser Ile Lys Ala
                355                 360                 365

Phe Asp Tyr Glu Lys Ala Tyr Ser Leu Gln Arg Pro Asn Asp His Glu
                370                 375                 380

Phe Met Gln Gln Pro Trp Thr Gly Phe Thr Val Gln Ile Ser Phe Val
385                 390                 395                 400

Lys Gly Trp Gly Gln Cys Tyr Thr Arg Gln Phe Ile Ser Ser Cys Pro
                405                 410                 415

Cys Trp Leu Glu Val Ile Phe Asn Ser Arg
                420                 425

(2) INFORMATION FOR SEQ ID NO:5:

(i) SEQUENCE CHARACTERISTICS:
         (A) LENGTH: 27 bases
         (B) TYPE:  nucleic acid
         (C) STRANDEDNESS:  single
         (D) TOPOLOGY:  linear (ii) MOLECULE TYPE:  other nucleic acid (xi) SEQUENCE DESCRIPTION: SEQ ID NO:5:

GTT NAR GTG NAC YTC NAK CCA GCA NGG                                     27

(2) INFORMATION FOR SEQ ID NO:6:

(i) SEQUENCE CHARACTERISTICS:
         (A) LENGTH:  9 amino acids
         (B) TYPE:  amino acid
         (C) STRANDEDNESS:  single
         (D) TOPOLOGY:  linear (ii) MOLECULE TYPE:  peptide (ix) FEATURE:
         (A) NAME/KEY:
         (B) LOCATION:
         (C) IDENTIFICATION METHOD:
         (D) OTHER INFORMATION: /note = "Xaa at position 4 is Leu or
             Ile"

(ix) FEATURE:
         (A) NAME/KEY:
         (B) LOCATION:
         (C) IDENTIFICATION METHOD:
         (D) OTHER INFORMATION: /note = "Xaa at position 6 is Val or Ile"
```

```
        (xi) SEQUENCE DESCRIPTION: SEQ ID NO:6:

Pro Cys Trp Xaa Glu Xaa His Leu Asn
 1               5

(2) INFORMATION FOR SEQ ID NO:7:

(i) SEQUENCE CHARACTERISTICS:
             (A) LENGTH:  27 bases
             (B) TYPE:  nucleic acid
             (C) STRANDEDNESS:  single
             (D) TOPOLOGY:  linear (ii) MOLECULE TYPE:  other nucleic acid (xi) SEQUENCE DESCRIPTION: SEQ ID NO:7:

GTA NYM NGS NCC CCA NCC YTT NAC RAA                              27

(2) INFORMATION FOR SEQ ID NO:8:

(i) SEQUENCE CHARACTERISTICS:
             (A) LENGTH:  8 amino acids
             (B) TYPE:  amino acid
             (C) STRANDEDNESS:  single
             (D) TOPOLOGY:  linear (ii) MOLECULE TYPE:  peptide (ix) FEATURE:
             (A) NAME/KEY:
             (B) LOCATION:
             (C) IDENTIFICATION METHOD:
             (D) OTHER INFORMATION: /note = "Xaa at position 7 is Ala, Pro,
                 Cys or Glu"

(xi) SEQUENCE DESCRIPTION: SEQ ID NO:8:

Phe Val Lys Gly Trp Gly Xaa Thr
 1               5

(2) INFORMATION FOR SEQ ID NO:9:

(i) SEQUENCE CHARACTERISTICS:
             (A) LENGTH:  27 bases
             (B) TYPE:  nucleic acid
             (C) STRANDEDNESS:  single
             (D) TOPOLOGY:  linear (ii) MOLECULE TYPE:  other nucleic acid (xi) SEQUENCE DESCRIPTION: SEQ ID NO:9:

CCATCCTAAT ACGACTCACT ATAGGGC                                    27

(2) INFORMATION FOR SEQ ID NO:10:

(i) SEQUENCE CHARACTERISTICS:
             (A) LENGTH:  23 bases
             (B) TYPE:  nucleic acid
             (C) STRANDEDNESS:  single
             (D) TOPOLOGY:  linear (ii) MOLECULE TYPE:  other nucleic acid (xi) SEQUENCE DESCRIPTION: SEQ ID NO:10:

ACTCACTATA GGGCTCGAGC GGC                                        23

(2) INFORMATION FOR SEQ ID NO:11:

(i) SEQUENCE CHARACTERISTICS:
             (A) LENGTH:  5 amino acids
             (B) TYPE:  amino acid
```

```
           (C) STRANDEDNESS:  single
           (D) TOPOLOGY:  linear (ii) MOLECULE TYPE:  peptide (xi) SEQUENCE DESCRIPTION: SEQ ID NO:11:

Lys Lys Leu Lys Glu
1               5

(2) INFORMATION FOR SEQ ID NO:12:

(i) SEQUENCE CHARACTERISTICS:
           (A) LENGTH:  5 amino acids
           (B) TYPE:  amino acid
           (C) STRANDEDNESS:  single
           (D) TOPOLOGY:  linear (ii) MOLECULE TYPE:  peptide (xi) SEQUENCE DESCRIPTION: SEQ ID NO:12:

Arg Trp Pro Asp Leu
1               5

(2) INFORMATION FOR SEQ ID NO:13:

(i) SEQUENCE CHARACTERISTICS:
           (A) LENGTH:  26 bases
           (B) TYPE:  nucleic acid
           (C) STRANDEDNESS:  single
           (D) TOPOLOGY:  linear (ii) MOLECULE TYPE:  other nucleic acid (xi) SEQUENCE DESCRIPTION: SEQ ID NO:13:

CCGGACGAGC GCAGATCGTT TGGTCC                                          26

(2) INFORMATION FOR SEQ ID NO:14:

(i) SEQUENCE CHARACTERISTICS:
           (A) LENGTH:  27 bases
           (B) TYPE:  nucleic acid
           (C) STRANDEDNESS:  single
           (D) TOPOLOGY:  linear (ii) MOLECULE TYPE:  other nucleic acid (xi) SEQUENCE DESCRIPTION: SEQ ID NO:14:

TTCATGCAGC AACCATGGAC GGGTTTC                                         27

(2) INFORMATION FOR SEQ ID NO:15:

(i) SEQUENCE CHARACTERISTICS:
           (A) LENGTH:  41 bases
           (B) TYPE:  nucleic acid
           (C) STRANDEDNESS:  single
           (D) TOPOLOGY:  linear (ii) MOLECULE TYPE:  other nucleic acid (xi) SEQUENCE DESCRIPTION: SEQ ID NO:15:

CCGCTAGCAC CATGTTCAGG ACCAAACGAT CTGCGCTCGT C                          41

(2) INFORMATION FOR SEQ ID NO:16:

(i) SEQUENCE CHARACTERISTICS:
           (A) LENGTH:  42 bases
           (B) TYPE:  nucleic acid
           (C) STRANDEDNESS:  single
           (D) TOPOLOGY:  linear
```

(ii) MOLECULE TYPE: other nucleic acid (xi) SEQUENCE DESCRIPTION: SEQ ID NO:16:

CCGGATCCTA TCGCGAGTTG AAGATGACCT CCAGCCAGCA CG                               42

(2) INFORMATION FOR SEQ ID NO:17:

(i) SEQUENCE CHARACTERISTICS:
           (A) LENGTH: 10 amino acids
           (B) TYPE: amino acid
           (C) STRANDEDNESS: single
           (D) TOPOLOGY: linear (ii) MOLECULE TYPE: peptide (xi) SEQUENCE DESCRIPTION: SEQ ID NO:17:

Glu Gln Lys Leu Ile Ser Glu Glu Asp Leu
 1               5                  10

(2) INFORMATION FOR SEQ ID NO:18:

(i) SEQUENCE CHARACTERISTICS:
           (A) LENGTH: 48 bases
           (B) TYPE: nucleic acid
           (C) STRANDEDNESS: single
           (D) TOPOLOGY: linear (ii) MOLECULE TYPE: other nucleic acid (xi) SEQUENCE DESCRIPTION: SEQ ID NO:18:

ATGTCTGAGC AGAAGCTGAT CTCTGAGGAA GACCTTGGAG CTAGCACC                        48

(2) INFORMATION FOR SEQ ID NO:19:

(i) SEQUENCE CHARACTERISTICS:
           (A) LENGTH: 465 amino acids
           (B) TYPE: amino acid
           (C) STRANDEDNESS: single
           (D) TOPOLOGY: linear (ii) MOLECULE TYPE: protein (vi) ORIGINAL SOURCE:
           (A) ORGANISM: Mus musculus
           (B) STRAIN: Swiss-Webster/NIH (xi) SEQUENCE DESCRIPTION: SEQ ID NO:19:

Met Asn Val Thr Ser Leu Phe Ser Phe Thr Ser Pro Ala Val Lys Arg Leu Leu
 1               5                  10                  15

Trp Lys Gln Gly Asp Glu Glu Lys Trp Ala Glu Lys Ala Val Asp Ala Leu
20                  25                  30                  35

Lys Lys Leu Lys Lys Lys Lys Gly Ala Met Glu Glu Leu Glu Lys Ala Leu Ser
40                  45                  50                  55

Pro Gly Gln Pro Ser Asn Cys Val Thr Ile Pro Arg Ser Leu Asp Gly Arg Leu
            60                  65                  70                  75

Val Ser His Arg Lys Gly Leu Pro His Val Ile Tyr Cys Arg Val Trp Arg Trp
                80                  85                  90                  95

Asp Leu Gln Ser His His Glu Leu Lys Pro Leu Glu Cys Cys Glu Phe Pro Phe
                100                 105                 110

Ser Lys Gln Lys Glu Val Cys Ile Asn Pro Tyr His Tyr Lys Arg Val Glu Ser
115                 120                 125                 130

Val Leu Pro Pro Val Leu Val Pro Arg His Ser Glu Tyr Asn Pro Gln His Ser
            135                 140                 145                 150

-continued

```
Leu Ala Gln Phe Arg Asn Leu Gly Gln Asn Glu Pro His Met Pro Leu Asn Ala
        155                 160                 165                 170

Phe Pro Asp Ser Phe Gln Gln Pro Asn Ser His Pro Phe Pro His Ser Pro Asn
        175                 180                 185                     190

Ser Tyr Pro Asn Ser Pro Gly Ser Ser Ser Thr Tyr Pro His Ser Pro Thr
        195                 200                 205

Ser Asp Pro Gly Ser Pro Phe Gln Met Pro Ala Asp Thr Pro Pro Ala Tyr
210             215                 220                 225

Pro Pro Glu Asp Pro Met Thr Gln Asp Gly Ser Gln Pro Met Asp Thr Asn Met
        230                 235                 240                 245

Ala Pro Pro Leu Pro Ser Glu Ile Asn Arg Gly Asp Val Gln Ala Val Ala Tyr
        250                 255                 260                 265

Glu Pro Lys His Trp Cys Ser Ile Val Tyr Tyr Glu Leu Asn Asn Arg Val Gly
        270                 275                 280                     285

Ala Phe His Ala Ser Ser Thr Ser Val Leu Val Asp Gly Phe Thr Asp Pro Ser
        290                 295                 300

Asn Lys Asn Arg Phe Cys Leu Gly Leu Leu Ser Asn Val Asn Arg Asn Ser Thr
305             310                 315                 320

Glu Asn Thr Arg Arg His Ile Gly Lys Gly Val His Leu Tyr Tyr Val Gly Gly
        325                 330                 335                 340

Val Tyr Ala Glu Cys Leu Ser Asp Ser Ser Ile Phe Val Gln Ser Arg Asn Cys
        345                 350                 355                 360

Tyr His His Gly Phe His Pro Thr Thr Val Cys Lys Ile Pro Ser Gly Cys Ser
        365                 370                 375                     380

Lys Ile Phe Asn Asn Gln Glu Phe Ala Gln Leu Leu Ala Gln Ser Val Asn His
                385                 390                 395

Phe Glu Thr Val Tyr Glu Leu Thr Lys Met Cys Thr Ile Arg Met Ser Phe Val
400                 405                 410                 415

Gly Trp Gly Ala Glu Tyr His Arg Gln Asp Val Thr Ser Thr Pro Cys Trp Ile
        420                 425                 430                 435

Ile His Leu His Gly Pro Leu Gln Trp Leu Asp Lys Val Leu Thr Gln Met Gly
        440                 445                 450                 455

Pro His Asn Pro Ile Ser Ser Val Ser
        460                 465
```